United States Patent
Noda et al.

[11] Patent Number: 5,476,447
[45] Date of Patent: Dec. 19, 1995

[54] INTRAPERITONEAL THERAPY APPARATUS

[75] Inventors: Kenji Noda, Sagamihara; Naomi Sekino, Tokyo; Yutaka Yanagawa, Tokyo; Takeo Usui, Tokyo; Kowji Tanikawa, Tokyo; Shiro Bitoh, Tokyo, all of Japan

[73] Assignee: Olympus Optical Co., Ltd., Tokyo, Japan

[21] Appl. No.: 312,503

[22] Filed: Sep. 26, 1994

Related U.S. Application Data

[63] Continuation of Ser. No. 83,993, Jun. 28, 1983, abandoned.

[30] Foreign Application Priority Data

| Jun. 30, 1992 | [JP] | Japan | 4-172605 |
| Oct. 16, 1992 | [JP] | Japan | 4-278588 |
| May 17, 1993 | [JP] | Japan | 5-114833 |
| May 17, 1993 | [JP] | Japan | 5-114837 |

[51] Int. Cl.⁶ .................................................. A61M 13/00
[52] U.S. Cl. ........................................................... 604/26
[58] Field of Search .................................. 604/20, 21, 23, 604/26, 35; 606/34, 37–40

[56] References Cited

U.S. PATENT DOCUMENTS

| 4,464,169 | 8/1984 | Semm | 604/26 |
| 4,676,774 | 6/1987 | Semm et al. | 604/26 |
| 4,735,603 | 4/1988 | Goodson et al. | 604/21 |
| 4,869,717 | 9/1989 | Adair | 604/26 |
| 5,085,657 | 2/1992 | Ben-Simhon | 604/30 |
| 5,139,478 | 8/1992 | Konincky et al. | 604/26 |
| 5,152,745 | 10/1992 | Steiner et al. | 604/23 |
| 5,171,311 | 12/1992 | Rydell et al. | 604/35 |
| 5,190,517 | 3/1993 | Zieve et al. | 604/38 |
| 5,199,944 | 4/1993 | Cosmesco | 604/26 |

FOREIGN PATENT DOCUMENTS

WO92/19168  11/1992  WIPO.

*Primary Examiner*—C. Fred Rosenbaum
*Assistant Examiner*—Manuel Mendez
*Attorney, Agent, or Firm*—Frishauf, Holtz, Goodman, Langer & Chick

[57] ABSTRACT

An intraperitoneal therapy apparatus for cauterizing tissues in a peritoneal cavity, which comprises a pneumoperitoneal device for introducing gas into the peritoneal cavity, thereby to inflate the cavity, a cautery device for cauterizing diseased tissues in the peritoneal cavity inflated by the pneumoperitoneal device, a suction device for removing fume from the peritoneal cavity, and a control circuit for controlling the pneumoperitoneal device and the suction device in accordance with an operation of the cautery device.

19 Claims, 8 Drawing Sheets

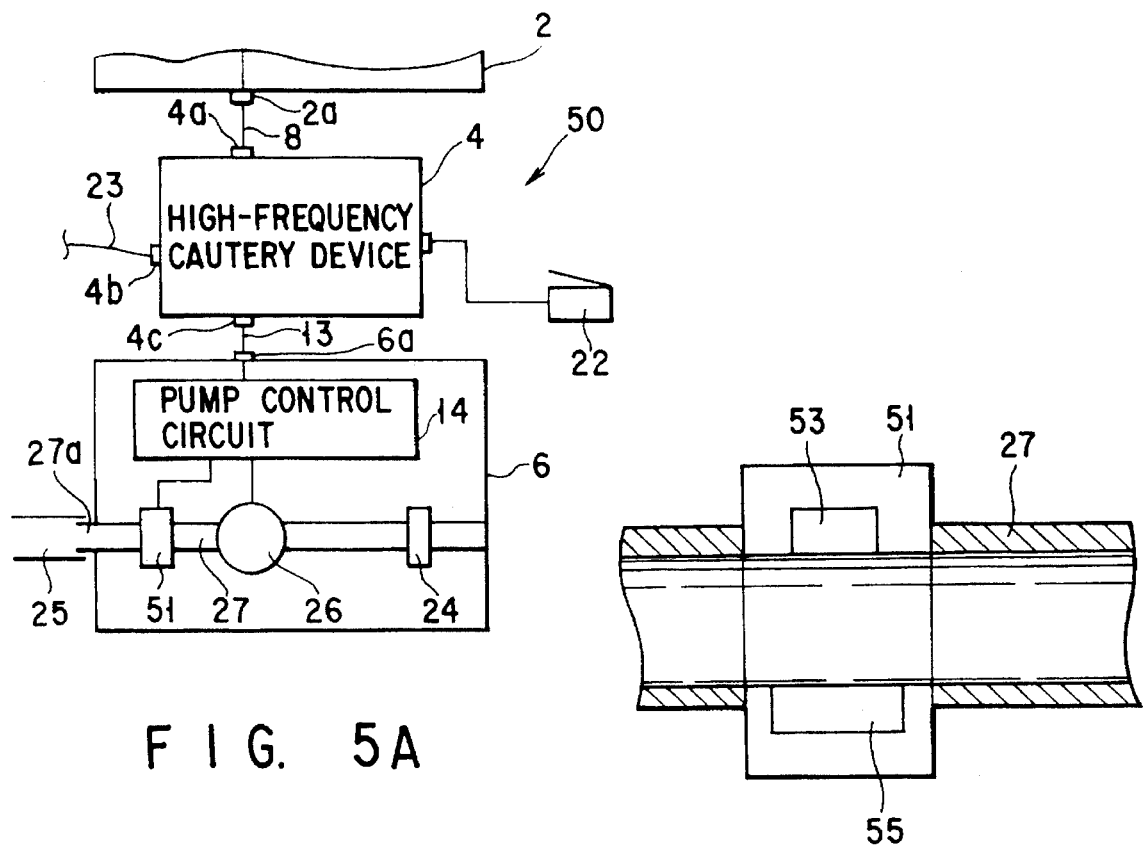
FIG. 5A
FIG. 5B
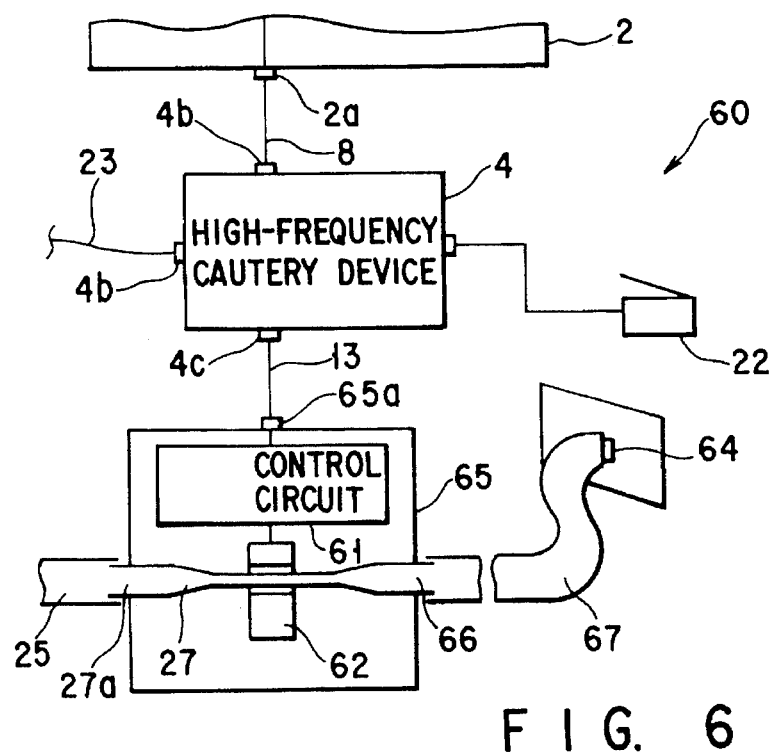
FIG. 6

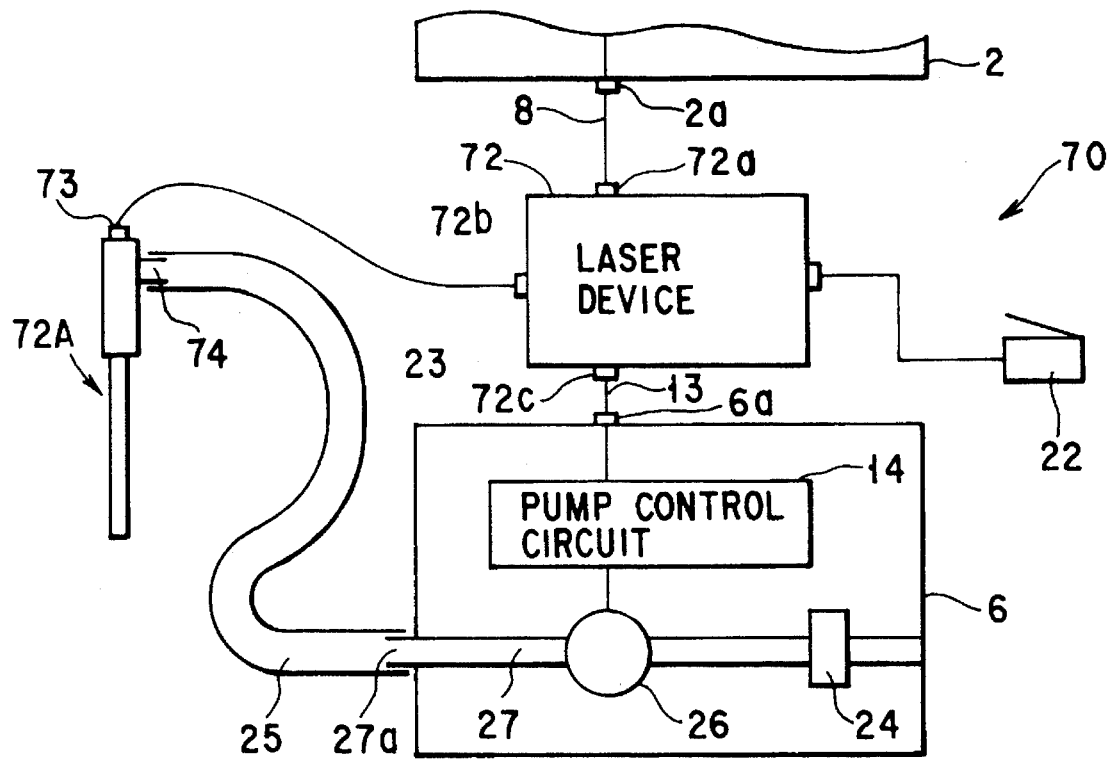
F I G. 7A
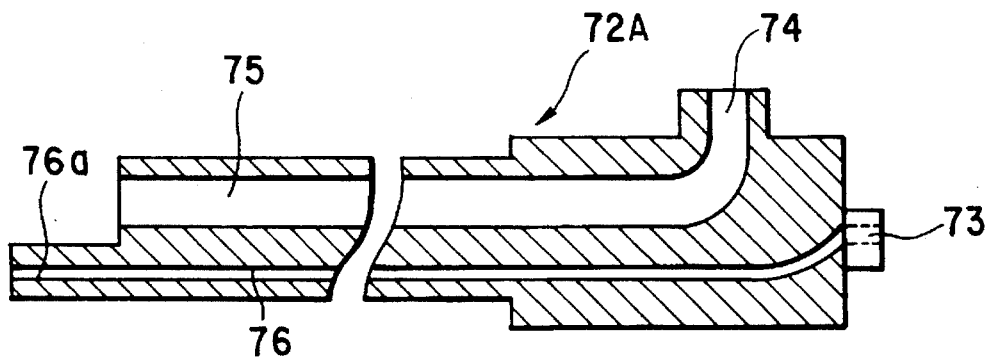
F I G. 7B

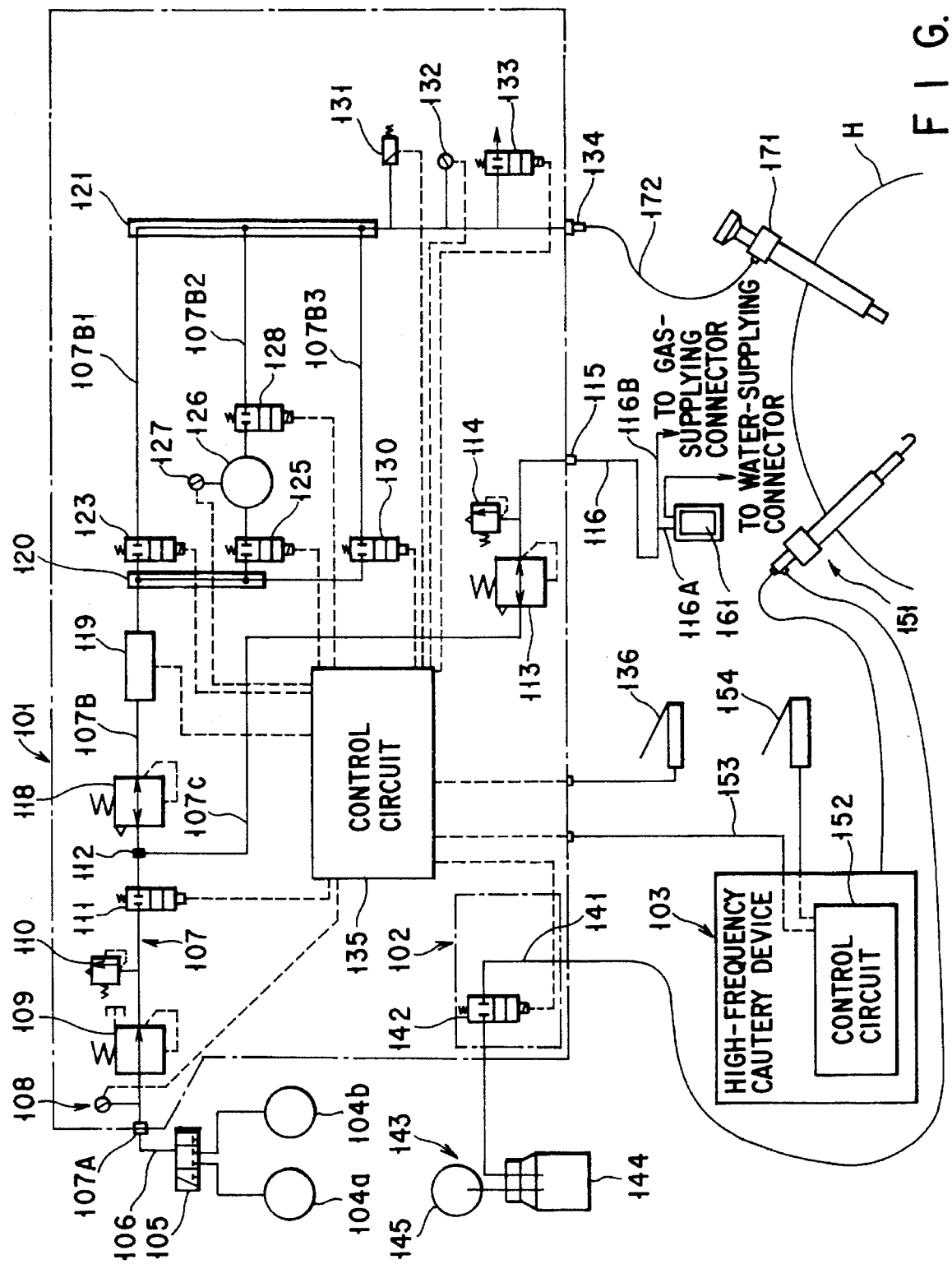

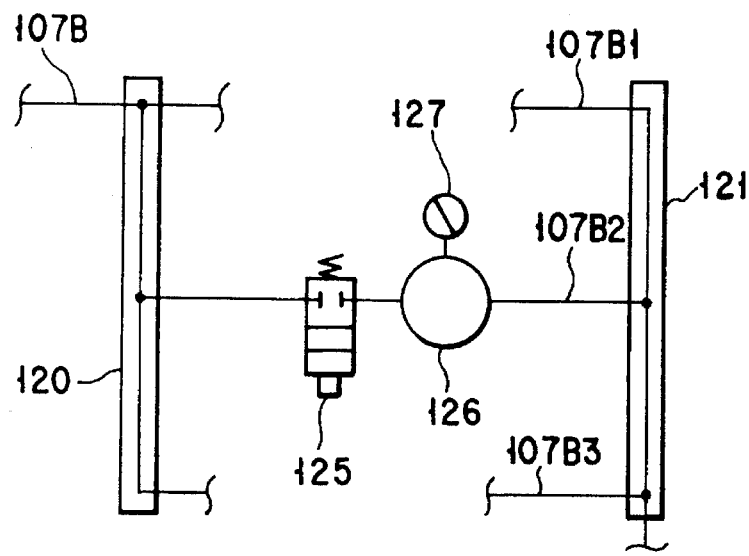
F I G. 11
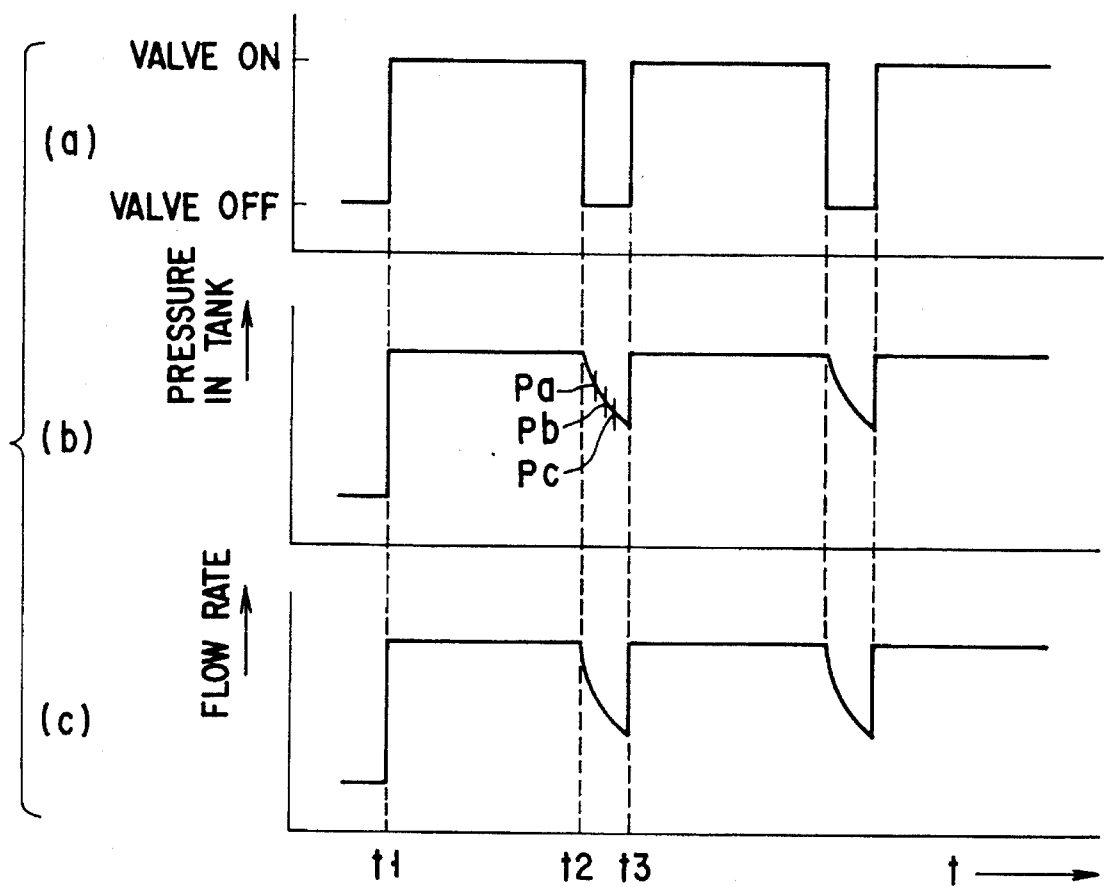
F I G. 12

INTRAPERITONEAL THERAPY APPARATUS

This application is a Continuation, of application Ser. No. 08/083,993, filed Jun. 28, 1993 and now abandoned.

BACKGROUND OF THE INVENTION

1. Field of the Invention

The present invention relates to an intraperitoneal therapy apparatus for performing pneumoperitoneum, inflating the peritoneal cavity of a patient, and for cauterizing diseased tissues within the inflated peritoneal cavity.

2. Description of the Related Art

Intraperitoneal therapy has been practiced widely, with the aid of endoscope. Recently, gallbladder extraction is often performed, while viewing the interior of the peritoneal cavity through an endoscope.

To achieve such a medical treatment, the peritoneal cavity is inflated so that a wide view field and a large space may be acquired for easy endoscopic operation. More precisely, $CO_2$ gas is supplied into the peritoneal cavity by means of a pneumoperitoneal device, thereby inflating the peritoneal cavity.

Diseased tissues in the peritoneal cavity, thus inflated, are cauterized by using a cautery device such as a high-frequency cautery device or a laser device, while observing the tissues through an endoscope. The tissues being cauterized emit fume. The fume may fill the peritoneal cavity will be so density that the interior of the cavity cannot be seen through the observation window of the endoscope.

In the event of fume-emission in the abdominal cavity, the cautery device is stopped. Then, the endoscope and other medical instruments are pulled out of the peritoneal cavity through the trocars piercing into the cavity. Next, the pneumoperitoneal device is driven, introducing $CO_2$ gas into the peritoneal cavity and naturally expelling the fume from the cavity via the trocars.

The fume may be removed from the peritoneal cavity by an alternatively method. For example, as is disclosed in German Patent Specification DE 37 06 717, the $CO_2$ gas and the fume are strongly pumped out of the peritoneal cavity, then they are passed through a disinfection filter, thus filtering out the fume, and the $CO_2$ is introduced back into the peritoneal cavity.

These fume-expelling methods are disadvantageous, however.

In the first method, it takes a relatively long time to expel the fume completely from the cavity. Inevitably the cautery device must be left unused for that long time, lengthening the time needed to complete the cautery, and the patient must suffer pain for a Long time. Further, the $CO_2$ is removed from the peritoneal cavity, along with the fume, reducing the intraperitoneal pressure and deflating the cavity. Consequently, pneumoperitoneum must be performed again to inflate the cavity to the initial state so that the therapy can continued.

In the second method, the flow rate at which the cleaned $CO_2$ gas is supplied back into the peritoneal cavity decreases due to the resistance the disinfection filter exhibits to the flow of the $CO_2$ gas. As a con sequence, the intraperitoneal pressure will fall, and the cavity will be deflated. To inflate the cavity to the initial degree, it takes a long period of time.

SUMMARY OF THE INVENTION

Accordingly, the object of the present invention is to provide an intraperitoneal therapy apparatus which can expel fume from a peritoneal cavity within a short time, without decreasing the intraperitoneal pressure.

To attain the object, there is provided an intraperitoneal therapy apparatus for cauterizing tissues in a peritoneal cavity, which comprises: pneumoperitoneal means for introducing gas into the peritoneal cavity, thereby to inflate the cavity; cautery means for cauterizing diseased tissues in the peritoneal cavity inflated by the pneumoperitoneal means; fume-expelling means for expelling fume from the peritoneal cavity; and control means for controlling the pneumoperitoneal means and the fume-expelling means in accordance with an operation of the cautery means.

While the cautery means is operating, the control means drives both the pneumoperitoneal means and the fume-expelling means in accordance with an operation of the cautery means. To be more explicit, the pneumoperitoneal means and the fume-expelling means are driven by the control means, expelling the fume from the peritoneal cavity at the rate which is substantially proportional to the thermal output of the cautery means.

In the peritoneal cavity, fume is generated in an amount substantially proportional to the thermal output of the cautery means. As described above, the rate at which the fume is expelled from the cavity by the pneumoperitoneal means and the fume-expelling means expel is substantially proportional to the thermal output of the cautery means. Hence, the intraperitoneal therapy apparatus can reliably expel the fume from the cavity, without reducing the intraperitoneal and within a short period of time. The time required to finish the intraperitoneal operation can thereby be shortened.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5A is a diagram schematically illustrating the fume-expelling system used in an intraperitoneal therapy apparatus which is a second embodiment of the present invention;

FIG. 5B is a schematic representation of the fume sensor used in the fume-expelling system shown in FIG. 5A;

FIG. 6 is a diagram schematically illustrating the fume-expelling system incorporated in an intraperitoneal therapy apparatus which is a third embodiment of this invention;

FIG. 7A is a diagram schematically illustrating the fume-expelling system used in an intraperitoneal therapy apparatus which is a fourth embodiment of the present invention;

FIG. 7B is a sectional side view of the medical instrument attached to the fourth embodiment of this invention;

FIG. 8 is a schematic representation of an intraperitoneal therapy apparatus according to a fifth embodiment of the present invention;

FIG. 11 is a diagram illustrating a first modification of the intraperitoneal pressure measuring pipe;

FIG. 12 is a timing chart for explaining how the modified pressure measuring pipe measures an intraperitoneal pressure.

DETAILED DESCRIPTION OF THE PREFERRED EMBODIMENTS

An intraperitoneal therapy apparatus, which is a first embodiment of the present invention, will be described with reference to FIGS. 1 to 4.

Figure 1:
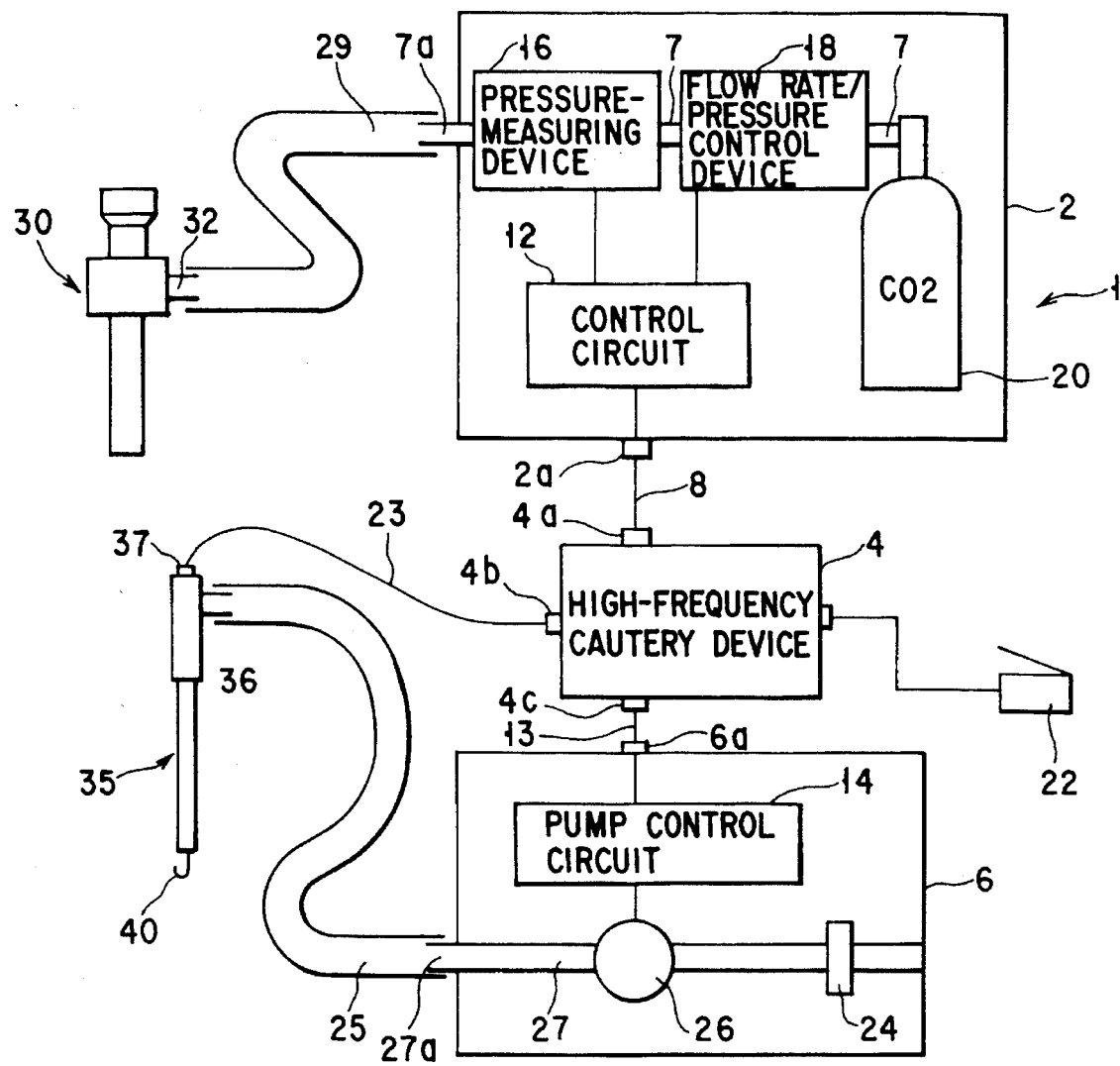
FIG. 1 is a schematic representation of an intraperitoneal therapy apparatus according to a first embodiment of the present invention.

As shown in FIG. 1, the therapy apparatus 1 comprises a pneumoperitoneal device 2, a high-frequency cautery device 4, and a suction device 6.

The pneumoperitoneal device 2 incorporates a cylinder 20 filled with $CO_2$ gas. The cylinder 20 is connected by an internal pipe 7 to a gas-supplying port 7a formed in one side of the pneumoperitoneal device 2. Hence, the $CO_2$ gas can be supplied from the cylinder 20 to the port 7a via the internal pipe 7. A pressure-measuring device 16 and a flow rate/pressure controller 18 are provided along the internal pipe 7. The device 16 is located more downstream than the controller 18, for measuring the pressure (i.e. intraperitoneal) in an peritoneal cavity which is to communicate with the internal pipe 7. The flow rate/pressure controller 18 is used to control the rate of supplying the $CO_2$ gas to the gas-supplying port 7a and the pressure of the $CO_2$ gas.

The pneumoperitoneal device 2 contains a control circuit 12, to which the pressure-measuring device 16 and the flow rate/pressure controller 18 are connected electrically. The circuit 12 is designed to control the flow rate/pressure controller 18 in accordance with the pressure measured by the pressure-measuring device 16 and the signal output by the high-frequency cautery device 4 and supplied via an input terminal 2a (later described).

A trocar 30 is connected to the pneumoperitoneal device 2 by a gas-supplying tube 29. The trocar 30 can be pierced into a peritoneal cavity through the abdominal wall. It has a hole through which to guide an endoscope or a medical instrument into the peritoneal cavity. The trocar 30 has a gas-supplying cap 32 projecting from the proximal end. The cap 32 is connected to one end of the gas-supplying tube 29, the other end of which is connected to the gas-supplying port 7a of the pneumoperitoneal device 2. The $CO_2$ gas supplied from the device 2 to the gas-supplying cap 32 via the gas-supplying tube 29 flows into the peritoneal cavity through, for example, the gap between the surface of the hole of the trocar 30 and the outer circumference of the endoscope or the medical instrument extending through the hole of the trocar 30.

As shown in FIG. 1, the high-frequency cautery device 4 is connected to the pneumoperitoneal device 2 by an output-signal line 8. More precisely, the output-signal line 8 is connected at one end to the input terminal 2a of the device 2 and at the other end to the first output terminal 4a of the cautery device 4. Electrically connected to the high-frequency cautery device 4, the pneumoperitoneal device 2 can operate in accordance with the signal output by the cautery device 4 as will be described later.

A foot switch 22 is connected to the high-frequency cautery device 4. When the switch 22 is treadled, the cautery device 4 will be driven.

The cautery device 4 has a second output terminal 4b. A cord 23 is connected at one end to the second output terminal 4b and at the other end to a medical instrument 35, thus electrically coupling the device 4 to the medical instrument 35. The medical instrument 35 has a suction cap 36 and an input terminal 37 at its proximal end. The input terminal 37 is connected to the cord 23.

Figure 2:
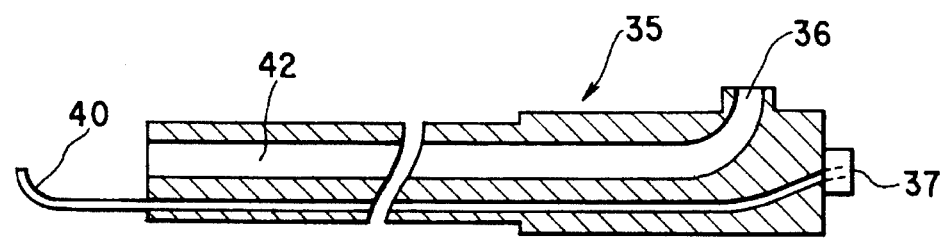
FIG. 2 is a sectional side view showing the medical instrument attached to the therapy apparatus shown in FIG. 1.

As shown in FIG. 2, the medical instrument 35 has a cautery electrode 40 and a suction hole 42. The cautery electrode 40 is embedded in the body of the instrument 35, projects from the distal end thereof, and is connected at its proximal end to the input terminal 37. The suction hole 42 opens at the suction cap 36 and at the distal end of the instrument 35. When the foot switch 22 is treadled, the high-frequency cautery device 4 is driven, applying a high-frequency output via the cord 23 to the cautery electrode 40 of the medical instrument 35.

The high-frequency cautery device 4 is connected by an output-signal line 13 to the suction device 6. To be more precise, the line 13 is connected at one end to the third output terminal 4c of the cautery device 4 and at the other end to the input terminal 6a of the suction device 6. The input terminal 6a is connected to the pump control circuit 14 incorporated in the suction device 6. Electrically connected to the cautery device 4, the pump control circuit 14 can control the vacuum pump 26 incorporated in the suction device 6, in accordance with the signal output by the cautery device 4.

In the suction device 6, the vacuum pump 26 is located halfway along a suction tube 27 as is shown in FIG. 1. The tube 27 has a suction port 27a at one end, which is connected to protrudes outward from the housing of the suction device 6. A suction tube 25 is connected at one end to the suction port 27a and at the other end to the suction cap 36 of the medical instrument 35.

Figure 3:
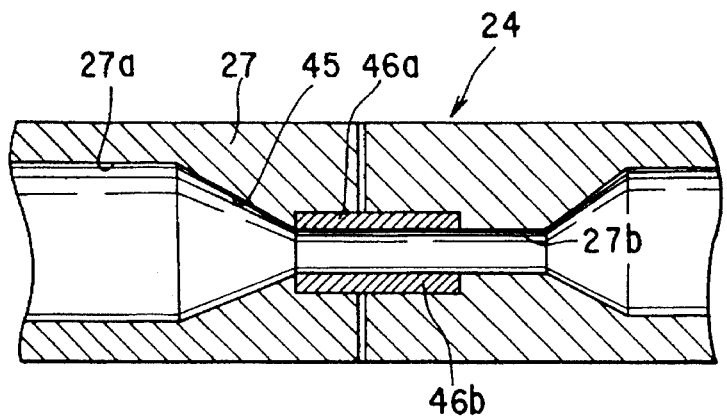
FIG. 3 is a sectional side view of the fume filter incorporated in the therapy apparatus shown in FIG. 1.

In the suction device 6, a fume filter 24 is located along the output part of the tube 27 as is illustrated in FIG. 1. As shown in FIG. 3, the filter 24 has an axial through hole which comprises a middle portion 27b, two end portions 27c, and two tapered portions 45. The end portions 27c have a diameter Larger that that of the middle portion 27b. The tapered portions 45 are located between the middle portion 27b and the first end portion 27c and between the middle portion 27b and the second end portion 27c, respectively.

A pair of metal electrodes 46a and 46b are mounted on that inner circumference of the filter 24 which is defined by the middle portion 27b of the through hole. The electrodes 46a and 46b oppose each other. When a high voltage is applied between the electrodes 46a and 46b, one of the electrodes attracts fume particles contained in the $CO_2$ gas passing through the middle portion 27b of the through hole of the fume filter 24. As a result, the filter 25 removes the fume from the $CO_2$ gas.

It will now be explained how the intraperitoneal therapy apparatus 1, described above, is operated to cauterize tissues in a peritoneal cavity.

First, the trocar 30 is inserted into the abdominal cavity through the abdominal wall. Next, the pneumoperitoneal device 2 is operated, supplying $CO_2$ gas from the gas cylinder 20 into the cavity through the trocar 30. The peritoneal cavity is thereby inflated. The pressure-measuring device 16 measures the intraperitoneal pressure, while the flow rate/pressure controller 18 controls the rate at which the $CO_2$ gas is introduced into the peritoneal cavity.

After the pressure in the peritoneal cavity reaches a predetermined value, an endoscope (not shown) and the medical instrument 35 are inserted into the peritoneal cavity through the trocar 30. While the intraperitoneal pressure being maintained at that predetermined value, the foot switch 22 is treadled, thereby actuating the high-frequency cautery device 4. As a result, a high-frequency current flows through the cautery electrode 40 which protrudes from the distal end of the medical instrument 35. The medical instrument 35 is manipulated, bringing the electrode 40 into contact with the diseased tissues in the peritoneal cavity. The tissues are thereby cauterized. As the tissues are cauterized, they emit fume.

At the same time the foot switch 22 is treadled, the high-frequency cautery device 4 generates and supplies a signal via the output-signal line 13 to the pump control circuit 14 incorporated in the suction device 6. The circuit 14 drives the vacuum pump 26 in accordance with the signal output by the cautery device 4. More specifically, the pump 26 draws gases at a rate which is proportional to the magnitude of the output signal of the cautery device 4. As a result, the fume emitted from the tissues cauterized is drawn, along with the $CO_2$ gas, from the peritoneal cavity through the suction tube 25 into the suction tube 27. The fume and the $CO_2$ gas pass through the fume filter 24. One of the electrodes 46a and 46b incorporated in the fume filter 24 attracts the fume particles. The fume is thereby filtered out, and the $CO_2$ gas only is discharged from the suction device 6.

As the $CO_2$ gas is drawn from the peritoneal cavity, together with the fume, the pressure in the cavity decreases. To compensate this pressure decrease, the foot switch 22 is treadled, driving the high-frequency cautery device 4. The cautery device 4 generates a signal of the same magnitude it has generated before. This signal is input to the control circuit 12 incorporated in the pneumoperitoneal device 2 through the output-signal line 8. In accordance with the signal the control circuit 12 controls the flow rate/pressure controller 18, which in turn controls the rate of introducing $CO_2$ gas into the peritoneal cavity. Thus, the pneumoperitoneal device 2 supplies $CO_2$ gas into the peritoneal cavity in an amount which is proportional to the magnitude of the signal output by the cautery device 4. In other words, the device 4 introduce $CO_2$ into the cavity in the same amount as the $CO_2$ discharged from the cavity along with the fume. Hence, the fume can be quickly expelled from the cavity, without reducing the intraperitoneal pressure.

Figure 4:
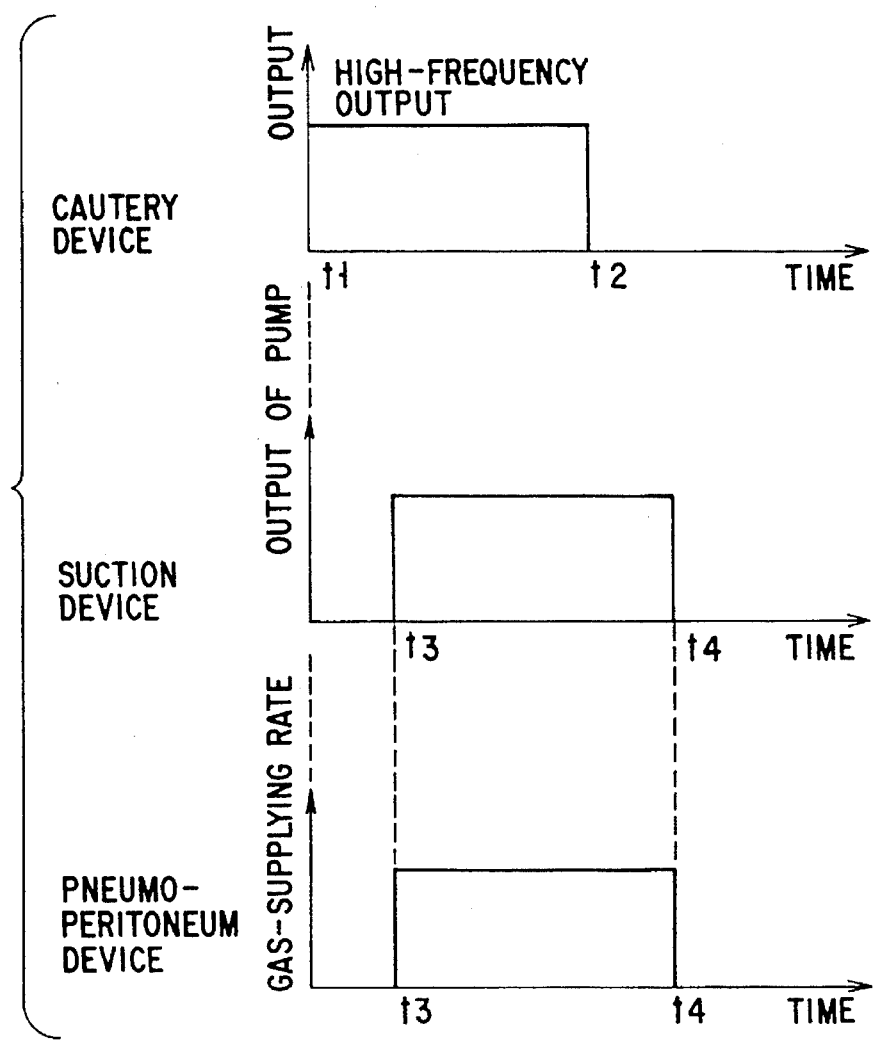
FIG. 4 is a timing chart for explaining the operation of the fume-expelling system used in the therapy apparatus of FIG. 1.

As can be understood from the timing charts of FIG. 4, the pneumoperitoneal device 2 and the suction device 6 are simultaneously driven at time $t_3$—upon lapse of a predetermined period ($t_3$-$t_1$) after the high-frequency cautery device 4 starts operating at time $t_1$, and are simultaneously stopped at time $t_4$—upon lapse of a predetermined period ($t_4$-$t_2$) after the cautery device 4 stops operating at time $t_2$. The pneumoperitoneal device 2 and the suction device 6 may be controlled in any other scheme. For example, the outputs of the devices 2 and 6 can be increased as the output signal of the cautery device 4 increases in magnitude.

As has been described, in the intraperitoneal therapy apparatus 1, the fume can be expelled from the peritoneal cavity as the tissues are cauterized, by operating only one switch, i.e., the foot switch 22, while pneumoperitoneum is being performed. Therefore, the fume can be expelled from the cavity both easily and quickly, without lowering the intraperitoneal pressure. Hence, the time required to cauterize the diseased tissues can be shortened.

An intraperitoneal therapy apparatus 50 according to a second embodiment of this invention will be described, with reference to FIGS. 5A and 5B.

The therapy apparatus 50 is characterized in that, as shown in FIG. 5A, the suction device 6 has a fume sensor 51 connected to the that part of the suction tube 27 which is located between the vacuum pump 26 and the suction port 27a, for detecting the fume flowing in the suction tube 27. In any other respect, the apparatus 50 is identical to the therapy apparatus 1, i.e., the first embodiment of the invention.

As shown in FIG. 5B, the fume sensor 51 comprises a light-emitting element 53 such as an light-emitting diode (LED) and a light-receiving element 55 such as a photodiode. The elements 53 and 55 are located in the suction tube 27, opposing each other. The element 53 emits a light beam to the element 55, which converts the beam into a current. Fume, if any, flowing in the suction tube 27 shuts off the light beam. As a result, the light-receiving element 55 ceases to output the current, whereby the fume sensor 51 detects the presence of fume.

As in the therapy apparatus 1 (FIG. 1), the pump control circuit 14 drives the vacuum pump 26 in accordance with the signal output by the high-frequency cautery device 4. Once after the cautery device 4 is stopped, however, the circuit 14 drives the vacuum pump 26 in accordance with the signal which the fume sensor 51 generates and which represents the presence or absence of fume in the the suction tube 27. To be more precise, even after the cautery device 4 is stopped, the suction device 6 continues to operate until the fume sensor 51 detects that fume has been expelled from the peritoneal cavity and no longer flows through the suction tube 27.

In the therapy apparatus 50, the suction device 6 may be operated independently of the high-frequency cautery device 4. More specifically, the vacuum pump 26 is driven under the control of the circuit 14, drawing the $CO_2$ gas at a low rate, until the fume sensor 51 detects fume passing through the suction tube 27. The moment the sensor 51 detects fume, the pump control circuit 14 drives the pump 26 faster, which starts drawing the $CO_2$ gas at a higher rate, thereby quickly expelling the fume from the peritoneal cavity. In this case, the pneumoperitoneal device 2 must, of course, be driven in accordance with the rate at which the suction device 6 draws the gas from the peritoneal cavity.

An intraperitoneal therapy apparatus 60 according to a third embodiment of the present invention will be described, with reference to FIG. 6.

This therapy apparatus 60 is characterized in that, the suction device 65 differs from the suction device 6 used in the first embodiment. More precisely, the device 65 has no component equivalent to the vacuum pump 26, and is connected to a suction unit (not shown) embedded in the wall of the operation room, which is installed in most clinics and hospitals. In any other respect, the apparatus 60 is identical to the therapy apparatus 1, i.e., the first embodiment of the invention.

The suction device 65 has a control circuit 61 and a pinch valve 62. The valve 62 is connected to the control circuit 61 and located halfway along the suction tube 27 as is shown in FIG. 6. The valve 62 is designed to squeeze and release the middle portion of the suction tube 27 under the control of the circuit 61, thereby to control the rate of the $CO_2$ gas flows through the suction tube 27. The suction tube 27 is connected to the suction unit. To be more explicit, its exhaust port 66 is coupled to one end of a connecting tube 67, other end of which is connected to the suction port 64 of the suction unit.

The suction device 65 has an input terminal 65a which is connected to the control circuit 61. The input terminal 65a is also connected to the high-frequency cautery device 4 by the output-signal line 13. The signal output by the cautery device 4 is thereby supplied to the control circuit 61 via the output-signal line 13 and the input terminal 65a. The control circuit 61 controls the pinch valve 62 in accordance with the output signal of the cautery device 4. More precisely, the greater the magnitude of the output signal of the device 4, the less the valve 62 squeezes the suction tube 27, increasing the rate at which the $CO_2$ gas flows through the tube 27.

The pinch valve 62 may be replaced by one which opens and closes the suction tube 27 completely. Nonetheless, the valve 62 is more desirable since it can gradually change the gas-flowing rate at the suction tube 27.

An intraperitoneal therapy apparatus 70 according to a fourth embodiment of the invention will be described with reference to FIGS. 7A and 7B.

The therapy apparatus 70 is characterized in that, as is shown in FIG. 7A, a laser device 72 is used in place of the high-frequency cautery device 4. In any other respect, the apparatus 70 is identical to the therapy apparatus 1, i.e., the first embodiment of the invention.

The laser device 72 has three output terminals 72a, 72b, and 72c which are equivalent to the terminals 4a, 4b, and 4c of the cautery device 4 incorporated in the first embodiment, respectively.

As shown in FIG. 7A, a medical instrument 72A is connected to the laser device 72 and the suction device 6. More precisely, the input terminal 73 of the instrument 72A is optically connected to the output terminal 72b of the laser device 72, and the suction cap 74 of the instrument 72A is coupled by a suction tube 25 to the suction port 27a of the suction device 6. As illustrated in FIG. 7B, the medical instrument 72A has a suction hole 75 and contains a laser-beam guiding fiber 76. The suction hole 75 is connected at its proximal end to the suction cap 74 and opens at its distal end in the vicinity of the distal end of the fiber 76. The laser-beam guiding fiber 76 is connected at its proximal end to the input terminal 73. The distal end of the fiber 76 is exposed at the distal end of the medical instrument 72A.

An intraperitoneal therapy apparatus according to a fifth embodiment of the invention will be described, with reference to FIG. 8.

As can be understood from FIG. 8, this therapy apparatus is characterized by a unit which is comprised of a pneumoperitoneal device and a suction device. The apparatus has a pneumoperitoneal device 101, a suction control section 102 incorporated in the device 101, and a high-frequency cautery device 103 connected to said unit.

The therapy apparatus further has two gas cylinders 104a and 104b. The cylinders 104a and 104b are connected to the gas-inlet port 107A of the pneumoperitoneal device 101 by a manual three-way valve 105 and a high-pressure hose 106. When the three-way valve 105 is manually operated, it connects either the cylinder 104a or the cylinder 104b to the pneumoperitoneal device 101.

The gas-inlet port 107A is connected to a pipe 107 which extends within the pneumoperitoneal device 101. Located along the pipe 107, from the upstream end (i.e., the gas-inlet port 107A) to the downstream end, are: a cylinder pressure sensor 108, a primary pressure-reducing device 109, a safety valve 110, and a valve 111. The sensor 108, which can measure pressures ranging from 0 to 100 $kgf/cm^2$, is electrically connected to a control circuit 135 located within the pneumoperitoneal device 101. The pressure the sensor 208 has measured is input to the control circuit 135 and displayed on a display panel (not shown) which is arranged on one side of the pneumoperitoneal device 101. The primary pressure-reducing device 109 is used to decrease the pressure under which the pneumoperitoneal gas is supplied from the cylinder 104a or 104b to the device 101, from about 60 $kgf/cm^2$ to about 3 $kgf/cm^2$. The safety valve 110 has an operating pressure of about 5 $kgf/cm^2$. The valve 111 is electrically connected to the control circuit 135, for opening and closing the pipe 107.

A first branching member 112 is connected to the downstream end of the pipe 107, which is located downstream of the valve 111. The member 112 has two down stream ports. Coupled to these ports are two branch pipes 107B and 107C.

A secondary pressure-reducing device 113 and a safety valve 114 are located along the second branch pipe 107C. The pressure-reducing device 113 is designed to reduce the pressure of the input gas to 350 mmHg. The safety valve 114 has an operating pressure of about 400 mmHg.

The downstream end of the second branch pipe 107C is connected to a coupler 115 to which an external tube 116 can be connected. The coupler 115 contains a valve which opens when the tube 116 is connected to the coupler 115, and closes when the tube 116 is disconnected from the coupler 115.

The tube 116 connected to the coupler 115 is forked into two branches 116A and 116B. The first branch 116A is coupled to a cuff bag 161 for pressurizing a bag containing physiological salt solution and connected to a water-supplying connector which is located in the sheath of an endoscope (not shown). The second branch 116B is coupled directly to a gas-supplying connector mounted on the sheath of the endoscope. A nozzle (not shown) protrudes from the distal end of the sheath, for washing the observation system contained in the distal end portion of the sheath. The water-supplying connector and the gas-supplying connector are connected to a tube which communicates with the nozzle.

Along the first branch pipe 107B, a secondary pressure-reducing device 118 and a flowmeter 119 are located, each connected to the pipe 107B. The secondary pressure-reducing device 118 reduces the input pressure to about 100 mmHg. The flowmeter 119 can measure flow rates ranging from 0 to 20 l/min. The flow meter 119 is electrically connected to the control circuit 153.

The first branch pipe 107B is connected to a second branching member 120 at the downstream side of the flowmeter 119. The member 120 has three downstream ports. Coupled to these ports are three branch pipes $107B_1$, $107B_2$, and $107B_3$. The downstream ends of these branch pipes $107B_1$, $107B_2$, and $107B_3$ are connected by a coupling member 121. The pipes $107B_1$, $107B_2$, and $107B_3$ are designed to allow the passage of gas at the flow rates of 2 l/min, 8 l/min, and 16 l/min, respectively.

A first valve 123 is connected to the third branch pipe

107B$_1$. The valve 123 is electrically connected to the control circuit 135. The circuit 135 controls the opening of the valve 123 such that gas flows in the third branch pipe 107B$_1$ at the constant rate of 2 l/min.

Figure 9:
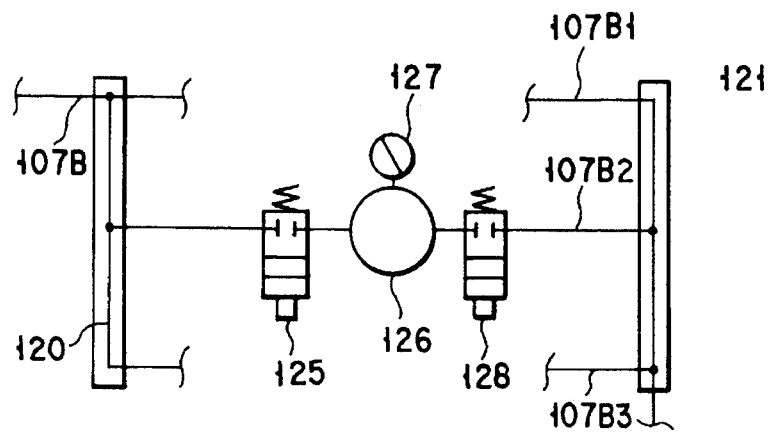
FIG. 9 is a diagram schematically showing the intraperitoneal pressure measuring pipe incorporated in the therapy apparatus shown in FIG. 8.

As shown in FIG. 9, a second valve 125, a tank 126, and a third valve 128 are connected to the fourth branch pipe 107B$_2$. The tank has a capacity of 300 cc. A first pressure gage 127 is coupled to the tank 126. The fourth branch pipe 107B$_2$ serves as gas-supplying pipe and functions to measure an intraperitoneal pressure. As shown in FIG. 8, the first valve 125, the first pressure gage 127, and the third valve 128 are electrically connected to the control circuit 135. The circuit 135 controls the opening of the third valve 128 such that gas flows in the fourth branch pipe 107B$_2$ at the constant rate of 8 l/min.

A fourth valve 130 is connected to the fifth branch pipe 107B$_3$. The fourth valve 130 is electrically connected to the control circuit 135. The circuit 135 controls the opening of the valve 130 such that gas flows in the fifth branch pipe 107B$_3$ at the constant rate of 16 l/min.

Connected to a downstream portion of the coupling member 121 which connects the branch pipes 107B$_1$, 107B$_2$ and 107B$_3$ together are: a pressure switch 131, a second pressure gage 132, and a pressure relief valve 133. The pressure switch 131, the second pressure gage 132, and the pressure relief valve 133 are connected to the control circuit 135. The downstream end of the first branch pipe 107B is coupled to a gas-supplying port 134.

A pneumoperitoneal tube 172 is connected at one end to the gas-supplying port 134. The other end of the tube 172 is connected to the trocar 171 inserted into a peritoneal cavity H. A foot switch 136 is connected to the control circuit 135 of the pneumoperitoneal device 101.

The suction control section 102 has a fume-expelling tube 141. A pinch valve 142 is connected to the middle portion of the tube 141, for opening and closing the fume-expelling tube 141. The pinch valve 142 is electrically connected to the control circuit 135. The proximal end of the tube 141 is coupled to a suction jar 144. The jar 144 is connected to a suction unit 145 installed in the wall of the operation room. The suction jar 144 and the suction unit 145 constitute a suction means 143. The distal end of the fume-expelling tube 141 is coupled to a medical instrument 151 which is inserted into the peritoneal cavity H. The instrument 151 is electrically connected to the high-frequency cautery device 103.

The high-frequency cautery device 103 comprises a control circuit 152. The control circuit 152 is connected by a signal line 153 to the control circuit 135 of the pneumoperitoneal device 101. The device 103 has a foot switch 154 which is connected to the control circuit 152.

The intraperitoneal therapy apparatus, i.e., the fifth embodiment of the invention, is operated in the following way.

First, a surgeon operates the operation panel (not shown) of the pneumoperitoneal device 101, thereby setting a target pneumoperitoneal pressure P$_0$ and a desirable flow rate of the pneumoperitoneal gas. When he or she pushes the start button on the operation panel, the device 101 starts supplying the pneumoperitoneal gas. Conversely, when he or she pushes the stop button on the operation panel, the device 101 stops supplying the gas.

Control of the gas supplying will be described. First, the surgeon measures the intraperitoneal pressure P$_1$ and compares it with the target pneumoperitoneal pressure P$_0$ he or she has set. In accordance with the difference between the pressures P$_1$ and P$_0$, the surgeon selects any one of the branch pipes 107B$_1$ to 107B$_3$ (i.e., the third to fifth branch pipes) branching from the first branch pipe 107B within the pneumoperitoneal device 101, and also sets a desirable time during which to open the valve 123, the valves 125 and 128, or the valve 130 to supply the pneumoperitoneal gas into the peritoneal cavity H. If the difference between the pressures P$_1$ and P$_0$ is relatively large, the fifth branch pipe 107B$_3$ is selected since this pipe 107B$_3$ allows the passage of the gas at a higher rate than the pipes 107B$_1$ and 107B$_2$l. If the pressure difference is relatively small, the third branch pipe 107B$_1$ is selected since the pipe 107B$_1$ allows the passage of the gas at a lower rate than the pipes 107B$_2$ and 107B$_3$l. In this case, pneumoperitoneum can be achieved with a higher accuracy. If the pressure difference is of an intermediate value, the fourth branch pipe 107B$_2$ is selected since the pipe 107B$_2$ allows the passage of the gas at an intermediate rate.

When the start button on the operation panel of the pneumoperitoneal device 101 is pushed, high-pressure CO$_2$ gas is supplied from the gas cylinder 104$a$ or the gas cylinder 104$b$ into the pipe 107 via the gas-inlet port 107A. The sensor 108 measures and indicates the pressure of the CO$_2$ gas. The primary pressure-reducing device 109 decreases the pressure of the CO$_2$ gas to about 3 bar. Should the device 109 fail to reduce the pressure, the safety valve 110 opens to discharge the high-pressure CO$_2$ gas, securing safety. The pressure (i.e., about 3 bar) of the CO$_2$ gas is further reduced to 100 mmHg by means of the secondary pressure-reducing device 118. The flowmeter 119 measures and indicates the gas-flowing rate at the first branch pipe 107B.

The tank 126 and the first pressure gage 127 cooperate, detecting the intraperitoneal pressure P$_1$ in accordance with a specific formula (later described). The data representing this pressure P$_1$, thus measured, is input to the control circuit 135. The control circuit 135 compares the intraperitoneal pressure P$_1$ with the preset target pneumoperitoneal pressure P$_0$, and the difference between these pressures P$_1$ and P$_0$ is multiplied by 0.2, thus calculating a value K. Namely:

$$K=(P_0-P_1)\times 0.2$$

From the value K thus obtained, the control circuit 135 selects any one of the branch pipes 107B$_1$ to 107B$_3$ (i.e., the third to fifth branch pipes) and determines the time during which to open the valve connected to the branch pipe selected. More precisely, the fifth branch pipe 107B$_3$ in which the gas flows at 16 l/min is selected if the value K is 1 or greater; the fourth branch pipe 107B$_2$ in which the gas flows at 8 l/min is selected if the value K is between 0.25 and 1; the third branch pipe 107B$_1$ in which the gas flows at 2 l/min is selected if the value K is 0.25 or less.

The time for which to open the valve of each branch pipe is determined in the following way. If the fifth branch pipe 107B$_3$ in which the gas flows at 16 l/min is selected, K is set as time for which to open the fourth valve 130. If the fourth branch pipe 107B$_2$ in which the gas flows at 8 l/min is selected, 2K is set as time for which to open the third valve 128. If the third branch pipe 107B$_1$ in which the gas flows at 2 l/min is selected, 8K is set as time for which to open the first valve 123. The longest time each valve can be opened is limited to 2 seconds.

When the difference, if any, between the target pneumoperitoneal pressure P$_0$ and the intraperitoneal pressure P$_1$ changes to, for example, 0.5 mmHg or less, the pneumoperitoneum is interrupted. Thereafter, the first pressure gage 127 continues to monitor the intraperitoneal pressure P$_1$.

The flow rate for each branch pipe can be set at a high level, a low level, or a variable level. If set at the variable level, the flow rate can be, on average, between 1 l/min and 10 l/min, changing in the units of 1 l/min. If set at the high level, the flow rate is 10 l/min on average. If set at the low level, the flow rate is 1 l/min on average.

In the case where the flow rate selected is small, the time for which to open the valve may be set shorter than the time determined from value K. For example, when the flow rate selected is 9 l/min, and the fifth branch pipe $107B_3$, in which the gas is flowing at 16 l/min, is therefore selected, the fourth valve 130 is opened for about 1.7 seconds and closed or about 1.3 seconds, whereby the average flow rate is 9 l/min. (The valve-opening time determined from value K is 2 seconds.)

Assume a pneumoperitoneal stylus which has a high gas resistance is coupled to the gas-supplying port 134. Even if the fifth branch pipe $107B_3$ is selected because it allows the passage of the gas at the rate of 16 l/min, the instantaneous flow rate reaches but only 4 l/min. The control circuit 135 controls the fourth valve 130 in accordance with the flow rate detected by the flowmeter 119. More specifically, the fourth valve 130 is opened for a longer time, 2 seconds at most.

Figure 10:
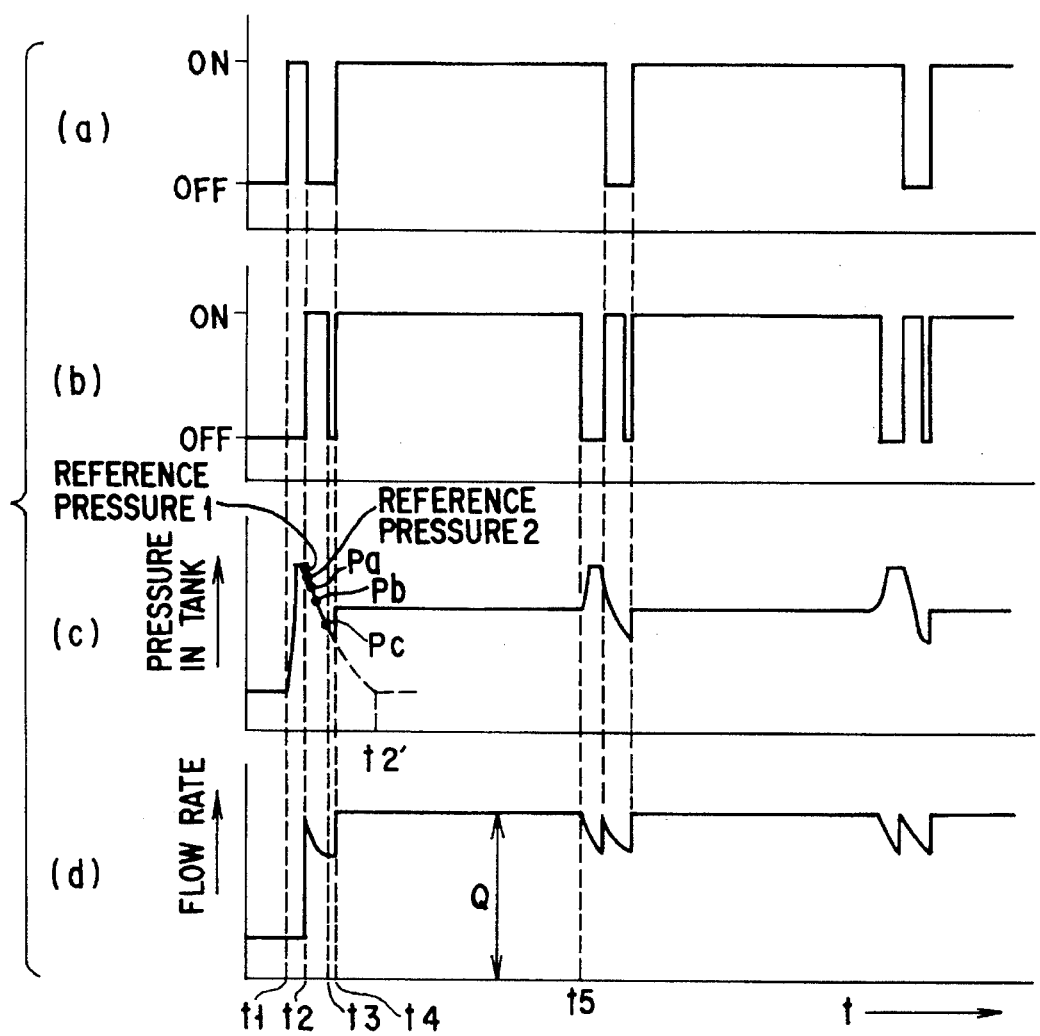
FIG. 10 is a timing chart for explaining how to measure an intraperitoneal pressure.
Figure 13:
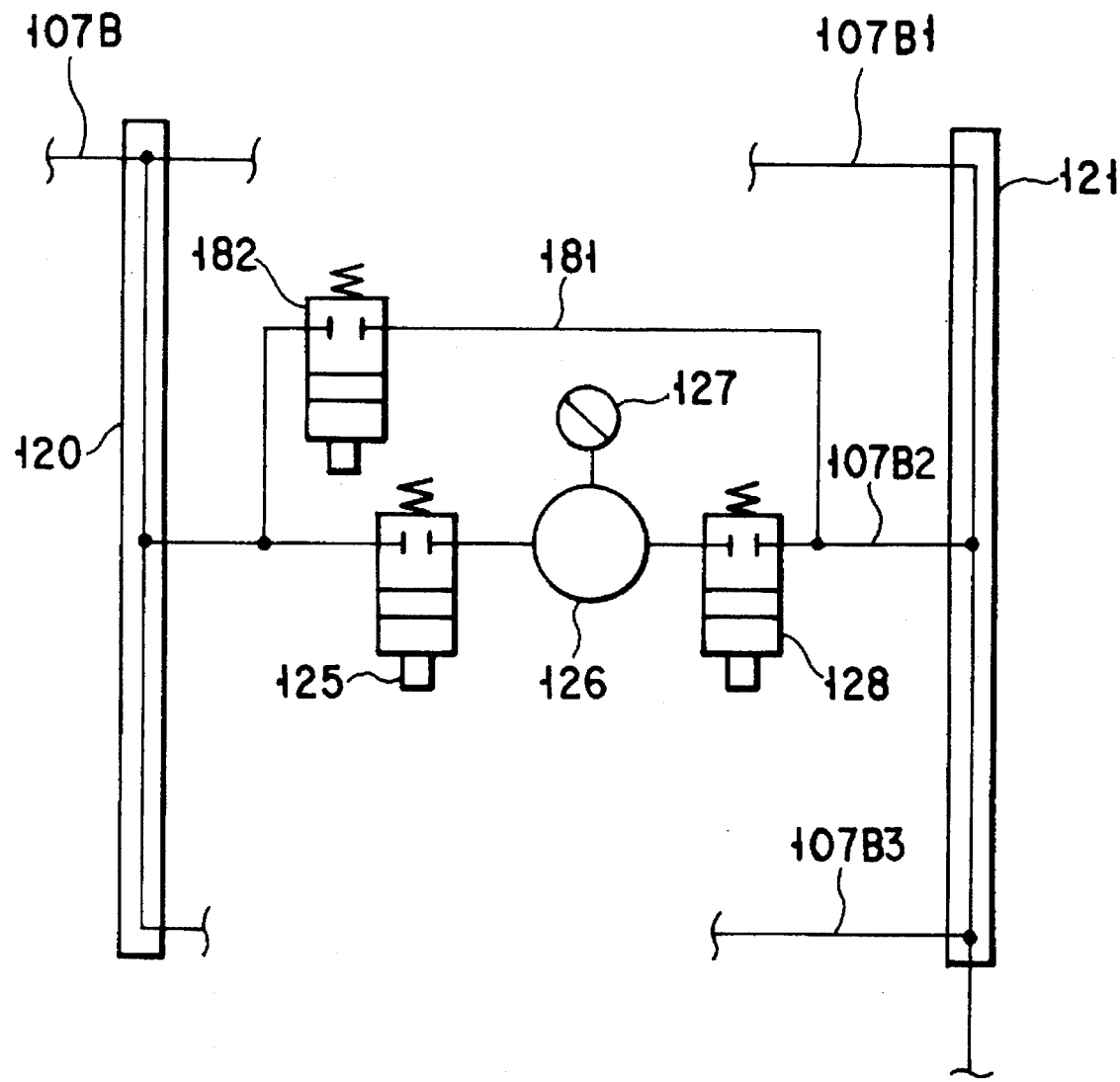
FIG. 13 is a diagram illustrating a second modification of the intraperitoneal pressure measuring pipe.

How to measure the intraperitoneal pressure $P_1$ will be explained with reference to the timing chart of FIG. 10. In FIG. 10, chart (a) illustrates how the second valve 125 is opened (ON) and closed (OFF), chart (b) shows how the third valve 128 is opened (ON) and closed (OFF), chart (c) represents how the pressure in the tank 126 changes with time, and chart (d) shows how the gas-flowing rate at the fourth branch pipe $107B_2$ changes with time.

First, the start button is turned on at time $t_1$, opening the second valve 125. The pressure in the tank 126 rises to 100 mmHg, i.e., the pressure at the output of the secondary pressure-reducing device 118. When the first pressure gage 127 detects at time $t_2$ that the pressure in the tank 126 has reached a predetermined maximum value of 90 mmHg, the second valve 125 is closed, and the third valve 128 is opened. As a result, the gas is released from the tank 126, lowering the pressure in the tank 126. The first pressure gage 127 detects this pressure decrease at three time points Pa, Pb, and Pc (FIG. 10 chart (c)). From the pressures measured by the gage 127 the control circuit 135 calculates the intraperitoneal pressure $P_1$. At the time $t_3$ the control circuit 135 closes the third valve 128, completing the measuring of the intraperitoneal pressure $P_1$.

The intervals among the pressure-measuring points Pa, Pb and Pc, which are equal, are set in accordance with the pressure-drop characteristic of the tank 126. More specifically, 80 mmHg and 60 mmHg are set for two reference tank pressures, whereas 90 mmHg is set as maximum pressure for the tank 126 as described above. The period elapsing from the time point reference value 1 and needed for the tank pressure to fall to the reference value 2 is measured. From the period measured, there is calculated the period between the points pa and Pb, which is equal to the period between the points Pb and Pc.

If the intraperitoneal pressure $P_1$ has not reached the preset target pneumoperitoneal pressure $P_0$, pneumoperitoneum is performed as follows.

At the time $t_4$, the second valve 125 and the third valve 128 are opened, introducing the $CO_2$ gas into the peritoneal cavity H. At the time $T_5$, the third valve 128 is closed, stopping the supply of the gas into the cavity H. This operation of opening and closing of the valves 125 and 128 is repeated until the intraperitoneal pressure $P_1$ increases to the target pneumoperitoneal pressure $P_0$. The interval between the times $t_4$ and $t_5$ is determined by the difference between the pressures $P_1$ and $P_0$; the larger the difference, the longer the interval. The moment the intraperitoneal pressure $P_1$ reaches the target pneumoperitoneal pressure $P_0$, the second valve 125 is closed, and the third valve 128 is opened. Thereafter, the first pressure gage 127 monitors the intraperitoneal pressure $P_1$.

If the intraperitoneal pressure $P_1$ falls below the preset target pressure $P_0$, the pneumoperitoneum is performed again. The period between the times $t_3$ and $t_4$ need not be provided. In other words, the control circuit 135 may close and open the third valve 128 virtually in no time, thereby measuring of the intraperitoneal pressure $P_1$ and introducing the $CO_2$ gas into the cavity H almost at the same time.

The minimum value for the interval between the times $t_4$ and $t_5$ is of such value that more gas flows into the peritoneal cavity H during the period between the times $t_4$ and $t_5$ than during the period between the times $t_2$ and $t_2'$ when the gas is released from the tank 126.

With the intraperitoneal therapy apparatus of FIG. 8, which is the fifth embodiment of the invention, it is possible to measure the intraperitoneal pressure $P_1$ without interrupting the gas-supply into the peritoneal cavity H through the trocar 171. This ensures efficient pneumoperitoneum. If the fourth branch pipe $107B_2$ in which the gas flows at 8 l/min is selected, the supplying of the $CO_2$ gas, performed by opening the valves 125 and 128 simultaneously, and the measuring the intraperitoneal pressure $P_1$ are carried out alternately.

When the foot switch 154 is treadled, the high frequency cautery device 103 supplies a high-frequency current to the electrode (not shown) of the medical instrument 151 which is inserted into the peritoneal cavity H. As a result, the electrode cauterizes the diseased tissues in the cavity H. While being cauterized, the tissues emits fume. How the fume is expelled from the peritoneal cavity H will be described. In particular, it will be explained how the pinch valve 142 of the suction control section 102 operates and how the pneumoperitoneal device 101 performs its function.

To expel fume from the peritoneal cavity H, the $CO_2$ is supplied at high rate into the cavity even if the intraperitoneal pressure $P_1$ has already reached the target value $P_0$, unlike during the pneumoperitoneum.

When the foot switch 154 is treadled, a signal having a magnitude proportional to the output preset for the cautery device 103 is supplied to the control circuit 135 incorporated in the pneumoperitoneal device 101. From the signal the control circuit 135 determines a proper gas-supplying rate and an appropriate gas-drawing rate. From the gas-supplying rate and the gas-drawing rate, the circuit 135 selects any one of the branch pipes $107B_1$, $107B_2$, and $107B_3$, determines the time for which to open the valve connected to the branch pipe selected, and determines conditions in which to operate the pinch valve 142.

First, the pinch valve 142 for drawing the gas is opened for a short time (e.g., about 0.5 seconds). As a result, the intraperitoneal pressure $P_1$ decreases. The pressure decrease is detected by the second pressure gage 132, whereby it is determined that the gas is being drawn from the cavity H. Then, $CO_2$ gas is introduced into and drawn from the peritoneal cavity H at the same time for a predetermined period (e.g., 1 second). Next, the intraperitoneal pressure $P_1$ is measured again by the second pressure gage 132. If the pressure $P_1$ measured is higher than the target pneumoperitoneal pressure $P_0$, the $CO_2$ gas is drawn from the cavity H for a longer time than before. If the pressure $P_1$ is lower than the target pressure $P_0$, the $CO_2$ gas is drawn from the cavity H for a shorter time than before. In either case, the intraperitoneal pressure $P_1$ is maintained at the target value $P_0$, while the fume is being expelled from the cavity H at high speed.

The gas-supplying time may be controlled by any other method. For instance, a flowmeter is coupled to the pipe in the suction control section 102, and the gas-flowing rate at the pipe is measured and compared with the value measured by the flowmeter 119 connected to the first branch pipe 107B. Then, the gas-supplying time is controlled such that the flow rates measured by the two flowmeter may be of the same value.

The control circuit 152 of the cautery device 103 may not be connected by the signal line 153 to the control circuit 135 of the pneumoperitoneal device 101, and the cautery device 103 needs to be operated independently of the pneumoperitoneal device 101. In such a case, the foot switch 136 is connected to the device 101 and treadled when fume is generated in the peritoneal cavity H, thereby to expel the fume from the cavity H. The gas is drawn from the cavity H, but at a fixed rate, however, irrespective of the magnitude of the output of the high-frequency cautery device 103. The fume-expelling tube 141 can be connected to the connection port (not shown) of the trocar 171, not to the medical instrument 151.

If the intraperitoneal pressure P1 is higher than the preset target value $P_0$, the suction control section 102 incorporated in the pneumoperitoneal device 101 will draw gas from the peritoneal cavity H in the following way.

Upon determining that the pressure $P_1$ becomes higher than the target value $P_0$ by a prescribed value (e.g., 5 mmHg) or more, the control circuit 135 drives the pinch valve 142, so that the suction means 143 may automatically draw the gas from the cavity H through the fume-expelling tube 141 of the suction control section 102. The suction means 143 continues to draw the gas until the intraperitoneal pressure $P_1$ reduces to the preset target value $P_0$.

The over-pressurizing of the peritoneal cavity H and the closing of the pneumoperitoneal tube 172 are distinguished from each other as follows.

The intraperitoneal pressure $P_1$ may increases to $P_0+5$ mmHg or more in two cases. First, the peritoneal cavity H is over-pressurized. Second, the gas in supplied into the cavity H while the pneumoperitoneal tube 172 is closed. Thus, when the pressure $P_1$ becomes higher than the target value $P_0$ by 5 mmHg or more, the control circuit 135 opens the pressure relief valve 133 for a predetermined time (e.g., 100 msec). The gas is thereby released from the pneumoperitoneal tube 172 in a small amount.

If the tube 172 is closed, the gas instantaneously flows out of that portion of the tube 172 which extends from the closed portion to the pressure relief valve 133, and the pressure detected by the second pressure gage 132 falls noticeably. On the other hand, if the peritoneal cavity H is over-pressurized, the pressure detected by the second pressure gage 132 scarcely falls even after the gas is thereby released from the pneumoperitoneal tube 172 in a small amount.

Hence, the over-pressurizing of the peritoneal cavity H and the closing of the pneumoperitoneal tube 172 can be distinguished from each other, from the pressure drop the second pressure gage 132 detects upon lapse of the predetermined time (e.g., 100 msec) during which the pressure relief valve 133 remains opened. If it is determined that the peritoneal cavity H is over-pressurized, the control circuit 135 generates an alarm and, at the same time, opens the pinch valve 142. As a result, the gas is drawn from the cavity H through the medical instrument 151 and the valve 142 by means of the suction means 143 which comprises the suction jar 144 and the suction unit 145. If it is determined that the fume-expelling tube 172 is closed, the control circuit 135 generates an alarm.

The intraperitoneal pressure $P_1$ is measured, primarily by the first pressure gage 127 which is connected to the tank 126. A decrease, if any, in the pressure in the tank 126 is related to the pressure drop detected by the second pressure gage 132 coupled to the pipe located downstream of the first branch pipe 107B. Therefore, both pressure gages 126 and 132 can be found to operate normally if the pressures they detect are the same. If the pressures the gages 126 and 132 detect are different, it is determined that either the gage 127 or the gage 132 is malfunctioning. In this case, the gas-supplying operation is interrupted.

If a pneumoperitoneal stylus is coupled to the gas-supplying port 134, the pressure in the upstream portion of the pipe 107 increases. This is because the stylus has a high gas resistance. If the pressure in the pipe 107 which the second pressure gage 132 detects is 50 mmHg or more, the gas-supplying rate at the pipe 107 is reduced, or the gas-supplying time is shortened. This measure taken, it is possible to prevent an accident such as the penetration of the stylus in the hypodermis, not piercing into the peritoneal cavity.

The pressure switch 131, which is coupled to a downstream portion of the coupling member 121, generates a signal if the gas pressure in the branch pipe $107B_1$, $107B_2$ or $107B_3$ rises above the pressure (e.g., 100 mmHg) at the output of the secondary pressure-reducing device 118. The signal is supplied to the control circuit 135, which generates an alarm. Thus, the pressure switch 131 functions as safety means.

Since the suction control section 102 is incorporated in the pneumoperitoneal device 101, the intraperitoneal therapy apparatus is more compact, and less tubes protrude from the housing of the device 101, than otherwise would be the case. The therapy apparatus can, therefore, be set up for use and put in order after use, with high efficiency.

FIG. 11 illustrates a modification of the intraperitoneal pressure measuring means comprising the fourth branch pipe $107B_2$ used in the fifth embodiment (FIG. 8). As can be understood from FIG. 11, as compared with FIG. 9, no component equivalent to the third valve 128 is connected to the pipe $107B_2$. The first pressure gage 127 detects a pressure drop in the tank 126 when the gas supply to the tank 126 is stopped, and measures the intraperitoneal pressure $P_1$ from this pressure drop. In accordance with the pressure $P_1$, thus measured, the control circuit 135 drives the second valve 125, thereby controlling the rate of supplying the gas into the peritoneal cavity. Hence, the pneumoperitoneal gas is introduced into the cavity to inflate the same appropriately.

It will be explained how the modified pressure measuring means operates, with reference to the timing charts (a), (b) and (c) of FIG. 12. In particular, it will be described how the second valve 125 regulates the gas pressure in the tank 126 and the gas flow rate in the fourth branch pipe $107B_2$. Chart (a) indicates when the second valve 125 is repeatedly opened (ON) and closed (OFF). Chart (b) shows how the gas pressure in the tank 126 changes with time. Chart (c) illustrates how the flow rate of $CO_2$ changes with time in the fourth branch pipe $107B_3$.

When the start button is pushed at time $t_1$, the control circuit 135 opens the second valve 125, whereby the pneumoperitoneal gas flows into the tank 126. The gas pressure in the tank 126 thereby increases, and the gas flows to the gas-supplying port 134 at an increased flow rate. At time $t_2$, or upon lapse of a predetermined time (e.g., 2 seconds), the control circuit 135 closes the second valve 125. Hence, the pneumoperitoneal gas no longer flows into the tank 126. The pressure in the tank 126 starts falling, decreasing the rate at which the gas is supplied to the gas-supplying port 134. The first pressure gage 127 measures the gas pressure changing in the tank 126 three times, at points Pa, Pb, and Pc. Data items representing the pressures measured at the points Pa, Pb and Pc are input to the control circuit 135. From the pressures the circuit 135 calculates the intraperitoneal pressure $P_1$. At time $t_3$, or upon lapse of a prescribed time (e.g., 0.5 seconds) from the time $t_2$, the control circuit 135 opens the second valve 125 again.

Thereafter, the control circuit 135 repeatedly opens, closes, and opens the second valve 125, thereby repeating the sequence of supplying the gas into the peritoneal cavity and measuring the intraperitoneal pressure $P_1$, as has been described in the preceding paragraph. In this process, the time of opening the valve 125 is shortened every time the pressure $P_1$ measured by the first pressure gage 127 approaches the target value $P_0$. The moment the intraperitoneal pressure $P_1$ the gage 127 measures reaches the target value $P_0$, the second valve 125 is closed, thus terminating the gas-supplying operation.

Since only one tank 126 suffices, the therapy apparatus has a simple structure and can be made more compact and manufactured at lower cost, than in the case where two or more tanks are required.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An intraperitoneal therapy apparatus for cauterizing tissues in a peritoneal cavity, comprising:

pneumoperitoneal means for introducing gas into the peritoneal cavity to inflate the cavity;

cautery means for cauterizing diseased tissues in the peritoneal cavity inflated by said pneumoperitoneal means;

fume-expelling means for expelling fumes from said peritoneal cavity; and control means for decreasing a gas flow rate in accordance with an increase in an intraperitoneal pressure when the intraperitoneal pressure becomes higher than a threshold value; and said control means further including means for decreasing a fume-expelling rate in accordance with a decrease in the intraperitoneal pressure when the intraperitoneal pressure becomes lower than a threshold value.

2. The intraperitoneal therapy apparatus according to claim 1, wherein said pneumoperitoneal means comprises:

a pneumoperitoneal device comprising a source of pneumoperitoneal gas for inflating the peritoneal cavity and a gas-supplying section connected to the source of pneumoperitoneal gas;

a gas-supplying tube having a gas inlet port connected to said gas-supplying section, and a gas outlet port for supplying the pneumoperitoneal gas;

a tubular guide having a distal end portion to be inserted into the peritoneal cavity through an abdominal wall, and a proximal end portion connected to said gas outlet port of said gas-supplying tube and to be located outside the abdominal wall; and gas-supplying means for supplying the pneumoperitoneal gas from said source of pneumoperitoneal gas the into the peritoneal cavity through said gas-supplying tube and said tubular guide.

3. The intraperitoneal therapy apparatus according to claim 1, wherein said cautery means includes a high-frequency cautery device having a cautery electrode protruding from a distal end of a medical instrument to be inserted into the peritoneal cavity, and wherein a high-frequency current is supplied to said cautery electrode while said cautery electrode is contacting body tissues, to thereby cauterize the contacted body tissues.

4. The intraperitoneal therapy apparatus according to claim 1, wherein said fume-expelling means comprises:

suction means having a coupling section to be connected to a suction port of a medical instrument to be inserted into the peritoneal cavity, an outlet section for discharging a fluid, and a suction passage extending between the coupling section and the outlet section.

5. The intraperitoneal therapy apparatus according to claim 4, further comprising a fume filter located in said suction passage.

6. The intraperitoneal therapy apparatus according to claim 5, wherein said fume filter includes a hollow cylindrical member having an inside diameter smaller than a diameter of said suction passage, and a pair of electrodes mounted on an inner circumference of said hollow cylindrical member and opposing each other, and wherein one of said electrodes attracts fume particles, as a high voltage is applied between said electrodes, thereby removing the fume particles from gas passing through said suction passage.

7. The intraperitoneal therapy apparatus according to claim 4, wherein said control means drives said suction means in accordance with a drive output of said cautery means, and simultaneously drives said pneumoperitoneal means such that said pneumoperitoneal means introduces into the peritoneal cavity the pneumoperitoneal gas in an amount corresponding to an amount of the gas which said suction means draws from the peritoneal cavity.

8. The intraperitoneal therapy apparatus according to claim 7, wherein said fume sensor comprises a light-emitting element and a light-receiving element located in said suction passage and opposing each other, and detects a presence of fumes in the gas passing through said suction passage, when light emitted from said light-emitting element to said light-receiving element is shut off.

9. The intraperitoneal therapy apparatus according to claim 1, wherein said fume-expelling means comprises:

suction means having a coupling section to be connected to a suction port of a medical instrument to be inserted into the peritoneal cavity, an outlet section for discharging a fluid, and a suction passage extending between the coupling section and the outlet section; and a fume sensor located in said suction passage, for detecting whether the gas passing through said suction passage contains fumes.

10. The intraperitoneal therapy apparatus according to claim 1, wherein said fume-expelling means comprises:

suction means having a coupling section to be connected to a suction port of a medical instrument to be inserted into the peritoneal cavity, an outlet section to be coupled to an external suction device, and a suction tube made of elastic material and extending between the coupling section and the outlet section;

a valve mounted at a middle portion of said suction tube for gradually squeezing and gradually releasing said suction tube, to thereby change a rate of drawing gas through said suction tube; and a control circuit for controlling said valve.

11. The intraperitoneal therapy apparatus according to claim 1, wherein said fume-expelling means comprises:

suction means having a coupling section to be connected to a suction port of a medical instrument to be inserted into the peritoneal cavity, an outlet section to be coupled to an external suction device, and a suction tube made of elastic material and extending between the coupling section and the outlet section;

a valve mounted at a middle portion of said suction tube for opening and closing said suction tube, to thereby change a rate of drawing gas through said suction tube; and a control circuit for controlling said valve.

12. The intraperitoneal therapy apparatus according to claim 1, wherein said cautery means includes a laser device for applying a laser beam to body tissues located within the peritoneal cavity through an optical fiber incorporated in a medical instrument inserted into the peritoneal cavity, to thereby cauterize the body tissues.

13. An intraperitoneal therapy apparatus according to claim 1, wherein said control means varies at least one of a flow rate of intraperitoneal gas and a flow rate of fume-expelling in accordance with an output from said cautery means.

14. An intraperitoneal therapy apparatus according to claim 1, wherein said threshold value is an intraperitoneal pressure set value in said pneumoperitoneal means.

15. A pneumoperitoneal apparatus which comprises a gas source, a gas-supplying pipe, a tank connected to a middle portion of the gas-supplying pipe, and in which pneumoperitoneal gas is supplied from the gas source through the tank into a peritoneal cavity to inflate the peritoneal cavity, and wherein an intraperitoneal pressure is determined from a pressure drop occurring in the tank when the pneumoperitoneal gas is released from the tank, and a rate of supplying the pneumoperitoneal gas into the peritoneal cavity is controlled in accordance with the intraperitoneal pressure determined, said apparatus further comprising:

a valve located in said gas-supplying pipe at least at an upstream position relative to said tank, for opening and closing said gas-supplying pipe; and a controller, responsive to a pressure upstream of said tank, for controlling a time for which said valve opens, such that more pneumoperitoneal gas passes through said tank than the pneumoperitoneal gas filled in said tank due to a pressure drop occurring upstream of said tank, and such that said valve is opened at all times except for a time when pressure in the peritoneal cavity is being checked.

16. The pneumoperitoneal apparatus according to claim 15, wherein said valve comprises first and second pipe opening/closing members which are located in said gas-supplying pipe upstream and downstream of sand tank, respectively.

17. The pneumoperitoneal apparatus according to claim 16, further comprising:

a bypass conduit having first and second ends coupled to said gas-supplying pipe, said first and second ends being respectively located upstream and downstream of said valve, said bypass conduit being arranged to supply the pneumoperitoneal gas at a higher rate than said gas-supplying pipe; and bypass conduit opening/closing means connected to said bypass conduit for selectively opening and closing said bypass conduit.

18. A pneumoperitoneal apparatus which comprises a gas source, a gas-supplying pipe, a tank connected to a middle portion of the gas-supplying pipe, and in which pneumoperitoneal gas is supplied from the gas source through the tank into a peritoneal cavity to inflate the peritoneal cavity, and wherein an intraperitoneal pressure is determined from a pressure drop occurring in the tank when the pneumoperitoneal gas is released from the tank, and a rate of supplying the pneumoperitoneal gas into the peritoneal cavity is controlled in accordance with the intraperitoneal pressure determined, said apparatus further comprising:

a valve located in said gas-supplying pipe at least at an upstream position relative to said tank, for opening and closing said gas-supplying pipe; and a controller, responsive to a pressure upstream of said tank, for controlling a time for which said valve opens, such that more pneumoperitoneal gas passes through said tank than the pneumoperitoneal gas filled in said tank due to a pressure drop occurring upstream of said tank; and wherein said valve comprises first and second pipe opening/closing members which are located in said gas-supplying pipe upstream and downstream of sand tank, respectively.

19. The pneumoperitoneal apparatus according to claim 18, further comprising:

a bypass conduit having first and second ends coupled to said gas-supplying pipe, said first and second ends being respectively located upstream and downstream of said valve, said bypass conduit being arranged to supply the pneumoperitoneal gas at a higher rate than said gas-supplying pipe; and bypass conduit opening/closing means connected to said bypass conduit for selectively opening and closing said bypass conduit.

* * * * *